United States Patent
de Juan, Jr. et al.

(10) Patent No.: US 6,676,607 B2
(45) Date of Patent: Jan. 13, 2004

(54) INTRAOPERATIVE MICROSURGICAL ULTRASONIC DEVICE AND METHODS RELATED THERETO

(75) Inventors: Eugene de Juan, Jr., Phoenix, MD (US); Patrick S. Jensen, Issaquah, WA (US)

(73) Assignee: The Johns Hopkins University, Baltimore, MD (US)

( * ) Notice: Subject to any disclaimer, the term of this patent is extended or adjusted under 35 U.S.C. 154(b) by 94 days.

(21) Appl. No.: 09/754,830

(22) Filed: Jan. 3, 2001

(65) Prior Publication Data

US 2001/0029335 A1 Oct. 11, 2001

Related U.S. Application Data

(60) Provisional application No. 60/174,260, filed on Jan. 3, 2000.

(51) Int. Cl.⁷ .................................................. A61B 8/14
(52) U.S. Cl. ........................ 600/461; 600/437; 600/452; 600/464; 600/466
(58) Field of Search ................................ 600/437–472; 351/200–247

(56) References Cited

U.S. PATENT DOCUMENTS

| | | | |
|---|---|---|---|
| 4,546,771 A | | 10/1985 | Eggleton et al. |
| 4,817,432 A | | 4/1989 | Wallace et al. |
| 5,152,293 A | | 10/1992 | Vonesh et al. |
| 5,308,355 A | * | 5/1994 | Dybbs ........................ 606/166 |
| 5,325,860 A | * | 7/1994 | Seward et al. .............. 600/425 |
| 5,375,602 A | | 12/1994 | Lancee et al. |
| 5,505,088 A | | 4/1996 | Chandraratna et al. |
| 5,588,432 A | * | 12/1996 | Crowley ...................... 600/439 |
| 5,938,612 A | * | 8/1999 | Kline-Schoder et al. .... 600/461 |
| 5,957,844 A | * | 9/1999 | Dekel et al. ................. 600/439 |
| 5,997,498 A | | 12/1999 | de Juan, Jr. |
| 6,019,724 A | * | 2/2000 | Gronningsaeter et al. ... 600/439 |

FOREIGN PATENT DOCUMENTS

| | | |
|---|---|---|
| EP | 0 353 209 A1 | 1/1990 |
| GB | 2 315 020 A | 1/1998 |

\* cited by examiner

*Primary Examiner*—George Manuel
*Assistant Examiner*—William C. Jung
(74) *Attorney, Agent, or Firm*—Peter F. Corless; Edwards & Angell, LLP

(57) ABSTRACT

Featured is a device that provides a mechanism for imaging structure and/or tissue of a surgical site during and after performing a microsurgical procedure such as ophthalmic surgical procedures. Also featured are methods and systems related thereto. In the imaging method of the present invention using such a device includes positioning a high frequency ultrasonic signal transmitting and receiving apparatus imaging mechanism in close proximity to the area to be scanned/imaged (e.g., surgical site), so that the high frequency ultrasonic signal penetrates the tissue/structure of the surgical site being scanned. The reflected ultrasonic signals, are processed so as to yield high quality/high resolution images of the scanned tissue/structure. Further, the high resolution images are evaluated by the surgeon during the procedure to determine if the surgical approach should be adjusted. If such a determination is made, then the planned surgical approach is adjusted to accommodate for any conditions not accounted for in the initial planning.

30 Claims, 5 Drawing Sheets

INTRAOPERATIVE MICROSURGICAL ULTRASONIC DEVICE AND METHODS RELATED THERETO

This application claims the benefit of U.S. Provisional Application Ser. No. 60/174,260 filed Jan. 3, 2000, the teachings of which are incorporated herein by reference.

FIELD OF INVENTION

The present invention relates to methods for performing surgery and instruments used therewith, in particular microsurgical methods and techniques and the instrumentalities used therewith to determine anatomical structure of the surgical site. The present invention more particularly relates to surgical methods involving the eye (e.g., retinal tear or detachment surgery, macular hole surgery) as well as the instruments or devices used during such surgical procedures to determine the physiological state of the tissue within the eye, such as the retina.

BACKGROUND OF THE INVENTION

The execution of microsurgical procedures, such as those involving the eye, is primarily driven by visual information available to the surgeon during the surgical procedure. For example, to aid in viewing the interior structures and regions of the eye when performing intraocular surgery, such as for example a retinal tear or detachment surgery and macular hole surgery, one or more surgical contact lenses are fitted into a lens ring that is sutured in place and spans the cornea. A cushion of transparent Healon or similar material is typically applied to the anterior surface of the eye to prevent corneal abrasion and to enhance optical clarity. In addition, a light source is introduced into the intra-ocular volume of the eye. The surgeon looks through the surgical contact lens and through the lens of the eye lens to observe the interior of the eye lighted by the light source.

Visual queues such as structure, color and the way the tissue responds to manipulation by a surgical instrument are used by the surgeon to determine anatomical structure and to make assumptions about the corresponding physiological state of the surrounding tissue. Based on these observations and assumptions, the surgeon develops a mental plan of a desired surgical approach. The surgeon then executes that plan manually. Unfortunately, in many microsurgical environments the visualization provided by existing optical microscopes is limited due to obstructed views or optical limitations.

Additionally, following execution of the plan, the surgeon typically evaluates the results or outcomes of the surgical procedure by means of such visual observations to determine if the procedure appears to be successful. Following eye surgery, the ophthalmic surgeon performs one or more diagnostics tests to determine the effectiveness of the surgical procedure. In a number of cases, however, the diagnostics test(s) performed show that the surgery was not as effective as indicated by the visual queues. Consequently, the patient again can be scheduled for surgery, whereupon the process is repeated. As a result, the patient experiences further risk for the additional surgery, experiences added discomfort because of the additional procedure(s) and increases the risk that the corrective action may be less than hoped for. Moreover, the added surgery results in increased cost to the patient or insurance carrier because of the additional corrective surgery.

There also are micro-surgical procedures such as those for example involving the middle ear, where the surgical site must be opened up or externalized in order for the surgeon to effectively visualize the surgical site. For example, in micro-surgical procedures involving the the middle ear, the middle ear is externalized (i.e., opened up) for the surgeon to observe the area.

There is disclosed in U.S. Pat. No. 5,152,295 an intra-operative diagnostic imaging device. This imaging device is in the form of a finger mounted probe and is disposed on a finger of the technician/doctor when imaging. Consequently, the use of this imaging device is limited to those situations in which the finger and finger mounted probe can access the area of interest. Such an imaging device, however, because of its physical size and arrangement cannot be used in the intraocular space of an eye.

There are ultrasonic imaging devices for ophthalmologic uses, however, such devices are external probes that are placed on an outside surface of the eye such as on the conjunctiva 4 (FIG. 1). In order for such external probes to view the retina, the ultrasonic sound must penetrate through several tissue layers (e.g., the cornea and the lens) and through approximately one inch of fluid in the intraocular space. Thus, a low frequency ultrasound wave (for example, on the order of 2 mHz) is used to image the retina. A low frequency must be used because higher frequencies are not capable of penetrating through to the retina. A low frequency ultrasonic signal, however, returns a low resolution image, whereas high frequency ultrasonic sound is capable of returning a high resolution image. Thus, fine detail of the retina is not available when using low frequency ultrasonic sound.

It thus would be desirable to provide a new imaging device and methods for performing micro-surgery that would allow the surgeon to intra-operatively image the surgical site and selected areas about the site. It would be particularly desirable to provide such an imaging device and such methods using an improved ultrasonic imaging technique that would provide intra-operative images of a higher quality in comparison to the images obtained with prior art ultrasonic imaging devices. It also would be desirable to provide such a device and methods that are particularly suited for providing high quality images of the anatomical structure of the eye such as the retina during the conduct of a surgical procedure as compared to the images using prior art ultrasonic devices. Such imaging devices preferably would be simple in construction and such methods would not require highly skilled users to utilize the device.

SUMMARY OF THE INVENTION

The present invention features a device that provides a mechanism for imaging structure and/or tissue of a surgical site during and after performing a microsurgical procedure such as ophthalmic surgical procedures. Such an intraoperative imaging device also allows a high frequency ultrasonic imaging mechanism to be disposed in close proximity to the area to be scanned/imaged (e.g., surgical site) so a surgeon is provided with high quality/high resolution images. The high quality/high resolution images provide a source of information to the surgeon that can be used to adjust the planned surgical approach so as to accommodate for any conditions not accounted for in the initial planning of the surgical approach to be taken.

An exemplary embodiment of the intra-operative imaging device includes a probe member having a predetermined length and an ultrasonic signal transmitting and receiving mechanism secured to the probe member. The predetermined length is established such that the ultrasonic signal transmitting and receiving mechanism is positioned in close proximity to the particular area or region to be scanned and disposed with a cavity of the body. In specific embodiments, the ultrasonic signal transmitting and receiving mechanism is an ultrasonic transducer, more particularly a high frequency ultrasonic transducer. The frequency of the ultrasonic signals is general established so the scanned image provides a desired amount of detail, particularly, as compared to the detail available when using prior art techniques, for the surgeon to evaluate the effectiveness of the procedure being performed and to make any adjustments to the procedure.

An imaging methodology according to the present invention includes steps of positioning an ultrasonic signal transmitting and receiving apparatus in proximity to a region to be scanned and performing an ultrasound scanning process using the ultrasonic signal transmitting and receiving mechanism during an in-process stage of a microsurgical procedure. Such a methodology includes providing an intra-operative imaging device of the present invention and inserting the probe member into a member of body such that the ultrasonic signal transmitting and receiving mechanism is proximal the region to be scanned for imaging. The method further includes evaluating the results of the scanning process performed and adjusting the surgical procedure/ approach when such evaluating determines that adjustment should be performed.

Also featured are micro-surgical procedures including surgical methods involving the eye, for example, retinal tear or detachment surgery and macular hole surgery. Further featured are device kits that comprise such intra-operative microsurgical devices alone or in conjunction with other microsurgical instruments such as entry alignment devices.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 2:
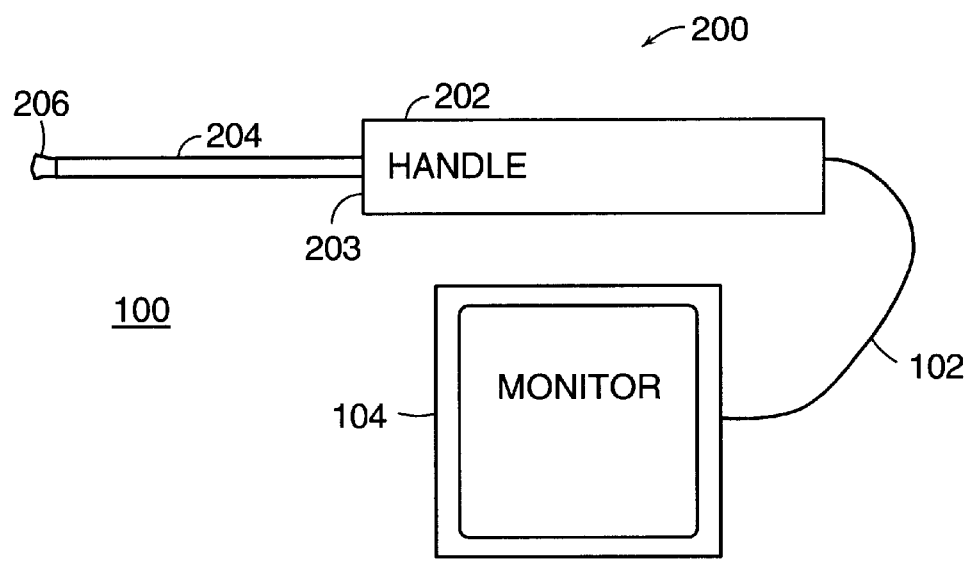
FIG. 2 is a schematic view of an ultrasonic viewing system including a intraoperative microsurgical device according to the present invention.
Figure 3:
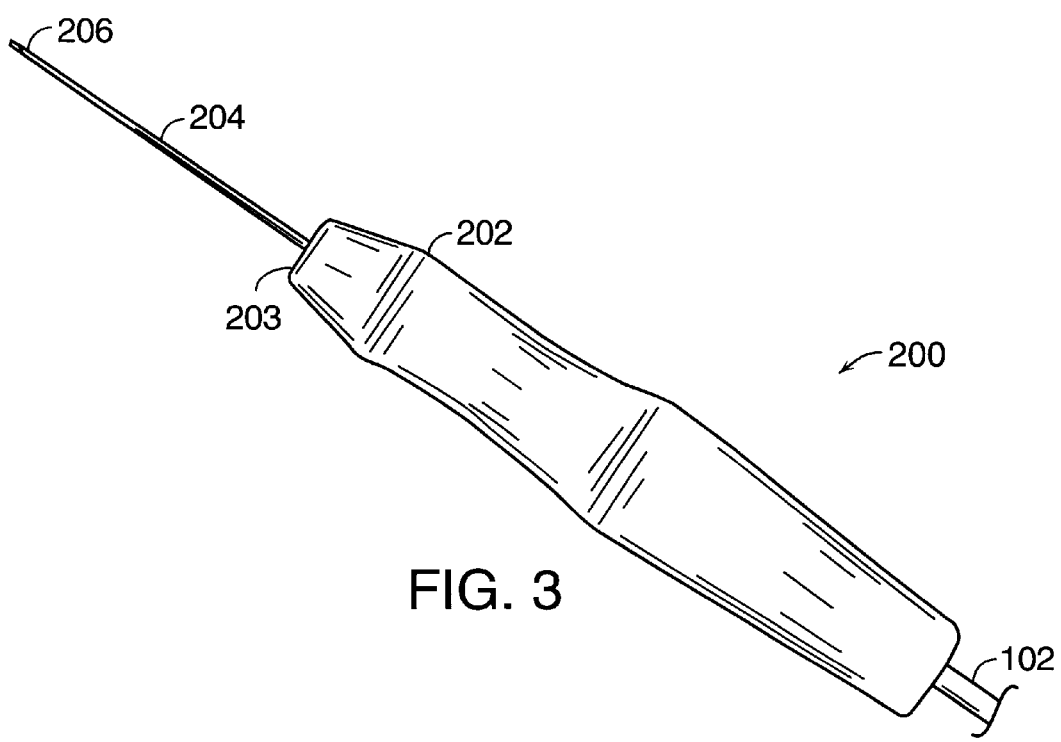
FIG. 3 is a top view of an intra-operative microsurgical device according to the present invention.

Referring now to the various figures of the drawing wherein like reference characters refer to like parts, there is shown in FIG. 2 a schematic view of an ultrasonic viewing system 100 including a intra-operative microsurgical device 200 according to the present invention. The intra-operative microsurgical device 200 includes a handle member 202, a probe member 204 and an ultrasonic transducer 206 affixed to the distal end of the probe member. In an illustrative embodiment, and as shown in FIG. 3, the handle member 202 is arranged and configured so as to allow the member to be gripped by a surgeon or technician that is performing the intra-operative ultrasonic scanning so as to provide an image of the scanned area.

This, however, shall not constitute a limitation as it is within the scope of the present invention for the intra-operative microsurgical device 200 to be held by or secured to a member (not shown) of an automated arm assembly or a manually operated arm assembly, each controlling the motion of the intra-operative microsurgical device. In such cases, the arm assembly provides a mechanism to control movement of the intra-operative microsurgical device 200 along predetermined and position determinable paths. Thus, a volume of material can be scanned and reconstructed for viewing and evaluation.

The handle member 202 also is constructed of any of a number of materials known to those skilled in the art that are appropriate for the intended use and structural loads imposed thereon during use. Such materials include metals such as stainless steel and plastics such as polymides.

Figure 5A:
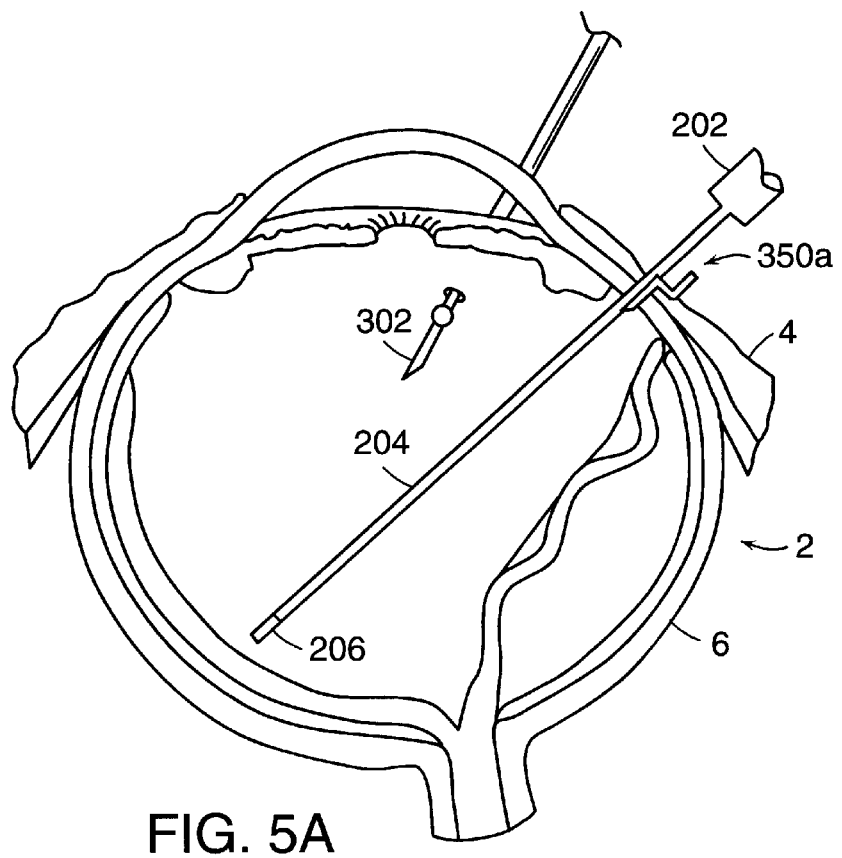
FIGS. 5A,B are cross-sectional schematic views of an eye undergoing a retinal tear repair procedure to illustrate use of the intra-operative microsurgical imaging device to image portions of the retina during the repair procedure.

The probe member 204 is secured to and extends from one end 203 of the handle member 202, more particularly, the probe member extends a predetermined distance or length from the handle member end so that the ultrasonic transducer 206 is remote from the handle member. The length also is set so that for a given application, the ultrasonic transducer 206 is disposable proximal the surgical cavity or site to be scanned and imaged. Further such a length is such that the handle member 202 is at a location where it can be grasped for manually or automated manipulation. In this way, the surgical cavity or opening in the body need not be sized to accommodate the handle member 202 or the mechanism for manual or automated manipulation. In an illustrative embodiment, the length of the probe member 204 is about 2.5 cm or larger so that the ultrasonic transducer 206 is proximal the back of the eye such as illustrated in FIGS. 5A,B. In an illustrative embodiment, the length of the probe member 204 is set so that the ultrasonic transducer 206 can be positioned about 0.5 mm from the surface of the retina.

In a more particular embodiment, the cross section of the probe member 204 transverse to the long axis of the probe member also is set so that the probe member is generally needle-like thereby minimizing the size of the opening in the body required to receive the probe member. In specific embodiments, the cross-sectional width of the probe member 204 is set so as to be about 1 mm or smaller and more specifically about 0.5 mm or 25 gauge. Such cross-sectional widths are particularly adaptable for use in imaging the anatomical structure of the eye. In an illustrative embodiment, the probe member 204 is a cylindrically shaped, however, other geometric shapes are contemplated and adaptable for use.

The ultrasonic transducer 206, is any of a number of devices, mechanisms or arrangements known to those skilled in the art that outputs an ultrasonic signal of a predetermined frequency, which is acoustically coupled to the area to be imaged, and receives the sound energy being reflected back by the material making up the area to be imaged. The ultrasonic transducer 206 also is preferably configured so that a high frequency signal is outputted and received by the transducer. In specific embodiments for high quality imaging, the ultrasonic transducer is configured so as to output a signal in the frequency range of about 20–100 mHz, more particularly in the range of about 40–70 mHz, more specifically to output a signal greater than or equal to about 50 mHz, or to output a signal of about 50 mHz.

Such frequencies are sufficient to provide high resolution information to the surgeon, information that is generally above and beyond what is currently possible using either conventional microscopes or conventional high resolution ultrasound imaging devices. Additionally, by setting the length of the probe member 204 to an appropriate length, the ultrasonic transducer 206 can be optimally positioned such that such high resolution imaging information can be obtained for structures relatively inaccessible to conventional high resolution ultrasound devices. Further, the capability of positioning the ultrasonic transducer 206 proximal the structure to be imaged, minimizes if not eliminates the short penetration depth characteristic of high frequency ultrasounds shortcoming of conventional externally located transducers or ultrasound probes.

Although the intra-operative imaging device 200 of the present invention is particularly configured for obtaining high quality or high resolution images, images having fine detail observable, such a use shall not be construed as a limitation. The ultrasonic transducer 206 is configurable to provide any available frequency appropriate for the tissue or material to be imaged for a given application, including frequencies lower than those provided above.

Each of the handle member 202 and the probe member 204 include a passage or lumen therein so that the ultrasonic transducer 206 can be operably coupled, electrically or optically, to the monitor 104 via the interconnecting cable 102. The interconnecting cable 102 is any of a number of cables known in the art to operably couple the output signals from the ultrasonic transducer 206 to the components, circuitry and devices making up the monitor 104. The monitor 104 is any of a number of apparatuses known to those skilled in the art which are capable of receiving output signals from an ultrasonic transducer and converting these signals into visual or computer useable output representative of the scanned image. Such a monitor 104 can include processing units and other components for storing and further manipulating the ultrasonic output signals and images for viewing.

In use, the ultrasonic transducer 206 returns A-scan information to the technician/surgeon, which information comprises the ultrasonic reflections from the tissues or structure beneath the ultrasonic transducer. As indicated above, during use the surgeon/technician manipulates the handle member 202 so as to cause the ultrasonic transducer 206 to move with respect to the surface of the area to be imaged/scanned. Typically, the surgeon/technician moves the ultrasonic transducer 206 at a slow rate to acquire a series of A-scans so as to form a line or slice of information. The surgeon/technician also can manipulate the handle member 202 so as to acquire a plurality of slices or lines of information displaced from each other or to acquire a matrix of A-scans, which can be re-constructed to form a volume of scanned tissue/structure.

The use of the intra-operative microsurgical imaging device 200 and the related methodologies of the present invention can be further understood from the following discussion concerning a method for treating a retinal tear or detachment by means of the laser photocoagulation technique and with reference to FIGS. 4A–C and FIGS. 5A,B.

Figure 1:
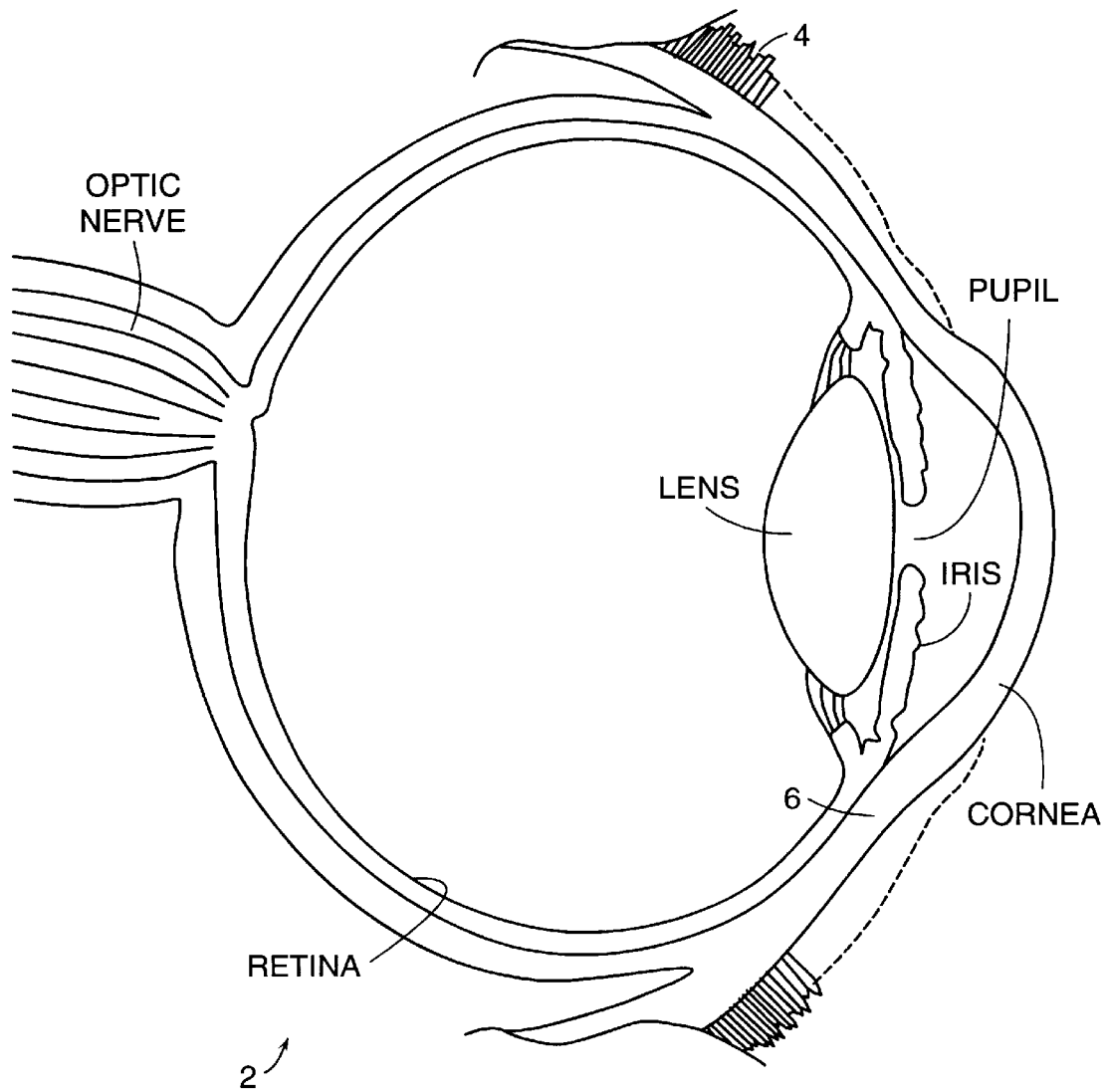
FIG. 1 is a cross-sectional schematic view of a non-diseased eye where the conjunctiva is pulled back for surgery, a conventional technique.
Figure 4C:
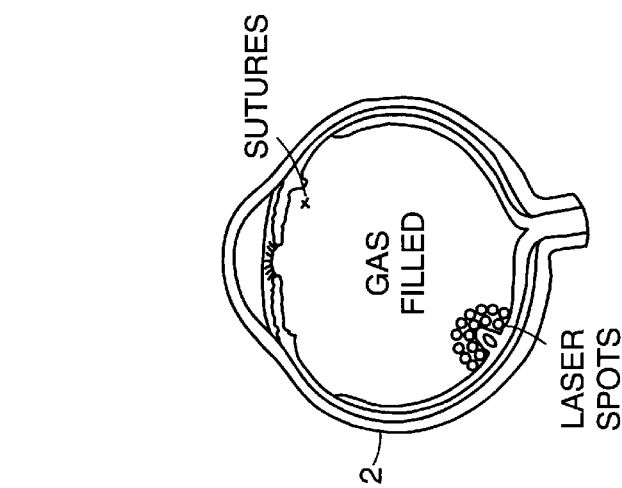
FIGS. 4A–C are cross-sectional schematic views of an eye undergoing a retinal tear repair procedure.
Figure 4B:
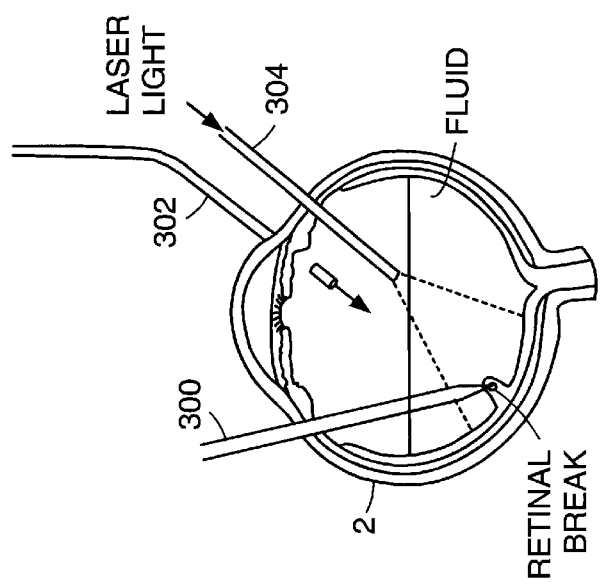
Figure 4A:
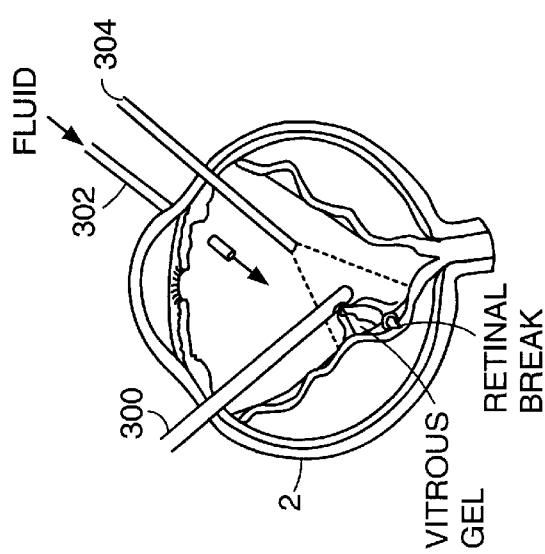

Reference also shall be made to FIGS. 1–3 for specific components or elements of the intra-operative microsurgical imaging device 200 of the present invention not otherwise shown in FIGS. 4A–C. In the following, the treatment or method for treating a retinal tear or detachment is described first in general terms and then in regards to performing intra-operative imaging using the intra-operative microsurgical imaging device 200 of the present invention. Reference also should be to co-pending application U.S. Ser. No. 09/523,767, filed Mar. 11, 2000 the teachings of which are incorporated herein by reference, for further details regarding the below described entry alignment devices and related methods.

In treating a retinal tear or detachment using the photo-coagulation technique employing a laser, a cutting/aspirating instrument 300, a cannula 302 and a light transmitting instrument 304 are inserted through the sclera so one end of each resides intraocular. The light transmitting instrument 304 is configured so the light from the laser (not shown) can be directed to specific locations on the retina. The cutting/aspirating instrument 300 is disposed so an end thereof is proximate the retinal tear.

Figure 5B:
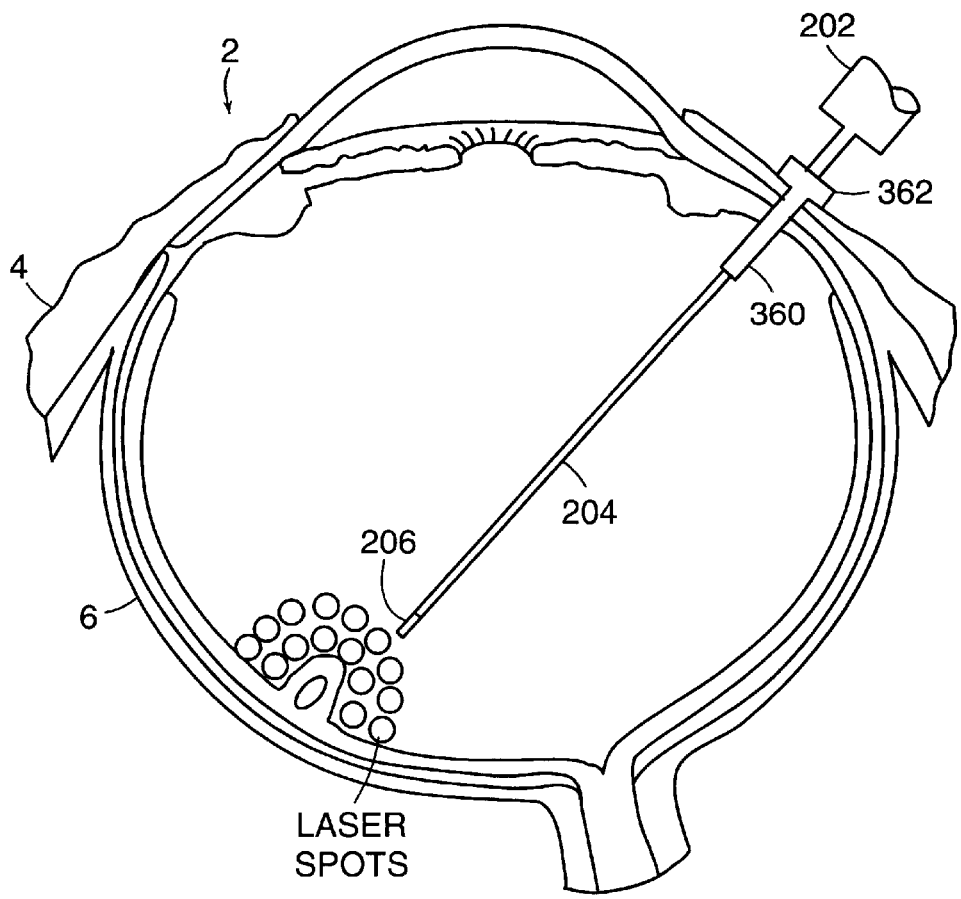

Alternatively, and as shown in FIGS. 5A–B, an entry alignment device 350a,b is used to provide or form an entry aperture in each of the conjunctiva and the sclera and to keep the apertures in each of the sclera and conjunctiva aligned during a procedure. As also illustrated, each of the cutting/aspirating instrument 300, the cannula 302 and the light transmitting instrument 304 can be received within the entry aperture formed by the entry alignment devices 350a,b.

Initially, the vitreous gel, especially all strands causing traction on the retinal tear are removed or aspirated by means of the cutting/aspirating instrument 300. As the vitreous gel is being aspirated, the intraocular volume is maintained by a continuous infusion of a fluid, such as a balanced salt solution (BSS), through the cannula 302. Any subretinal fluid is also aspirated through the retinal tear. Thereafter, the vitreous fluid is aspirated and exchanged with a gas such as air passing through the cannula 302. As taught in U.S. Pat. No. 5,997,498, the teachings of which are incorporated herein by reference, the gas or air being exchanged is humidified by means of an in-line humidifier and humidification system as described therein.

The retina surrounding the tear is then repeatedly exposed to the laser light from the light transmitting instrument 304 so as to form a plurality of heat spots on the retina surrounding the retinal tear. In particular, the practitioner manipulates the light transmitting instrument 304 so that a plurality of rows of a plurality of such heat spots surrounds the retinal tear. In this way, the retinal tear is photocoagulated with a laser to achieve a thermal adhesive injury. The heat spots also produce scars that prevent fluid from passing through and collecting under the retina.

Thereafter, the intraocular gas or air, infused while exposing the retina surrounding the retinal tear to laser light, is totally exchanged for a longer-lasting gas, such as sulfur hexafluorine or perfluoro propane. This gas allows an adequate tamponade time for the therapeutic chorioretinal scar to develop. Preferably, the longer lasting gas being infused is humidified using the in-line humidifier as described above. After completing the "in eye" portion of the treatment procedure, the inserted instruments and cannula are removed from the eye.

In the present invention, the intra-operative microsurgical imaging device 200 can be utilized at various times during a surgical procedure to provide additional information regarding the microsurgical environment including anatomical structural information and the effectiveness of the surgical approach being executed by the surgeon. There is shown in FIGS. 5A,B cross-sectional schematic views of an eye undergoing the retinal tear repair procedure of FIGS. 4A–C to illustrate use of the intra-operative microsurgical imaging device 200 to image portions of the retina.

Figures 6A, 6B:
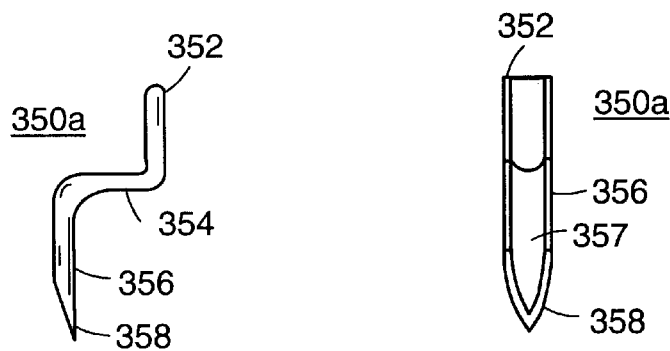
FIGS. 6A,B are front and side views of the entry alignment device of FIG. 5A.
Figure 6C:
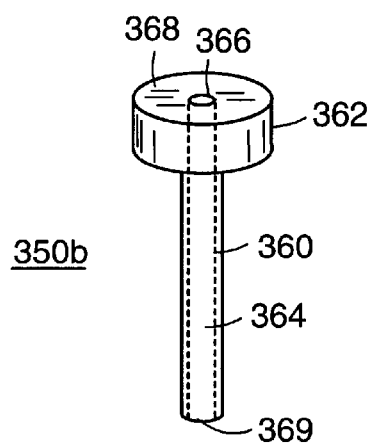
FIG. 6C is a perspective view of the entry alignment device of FIG. 5B.

Referring now to FIG. 5A, there is shown the use of the intra-operative microsurgical imaging device 200 at some point during the repair procedure. In the illustrated embodiment, an entry alignment device 350a (see also FIGS. 6A,B) is inserted through the conjunctiva and the sclera to form an entry aperture. As shown more clearly in FIG. 6B, the inserted portion 356 of the entry alignment device 350a is configured so as to include a dished portion 357 that extends between the stop portion 354 and the pointed end 358. Thus, the exterior surfaces of the probe member 204 are received in the dished portion 357 so as to guide the probe member and the ultrasonic transducer 206 through the conjunctiva 4 and the sclera 6 into the intra-ocular volume as they are being inserted.

Referring now to FIG. 5B, there is shown the use of the intra-operative microsurgical imaging device 200 after performing the photocoagulation of the retina according to the repair procedure. In the illustrated embodiment, another entry alignment device 350b (see also FIGS. 6A,B) is inserted through the conjunctiva 4 and the sclera 6 to form an entry aperture. This entry alignment device 350b includes an insertion member 360 and a stop member 362 that is affixed about the exterior of the insertion member 360. The entry alignment device 350b of this embodiment is configured and arranged so that in use, the portion of the insertion member 360 that is below the stop member 362 is passed through each of the conjunctiva 4 and the sclera 6. Additionally, in use the entry alignment member 350b is inserted until the stop member 362 is proximal the exterior surface of the eye 2 similar to that shown for the stop portion 354 in FIG. 6A.

In the illustrated embodiment, an end of the insertion member 360 is securably received in the stop member 362. Alternatively, the entry alignment device is constructed such that the insertion and stop members 360, 362 form an integral structure. In yet another embodiment, the insertion member 360 and stop member 362 are configured and arranged so the insertion member extends through an aperture in the stop member. In this case an end of the insertion member is disposed proximal an end surface 368 of the stop member or the insertion member extends outwardly from the stop portion end surface. The insertion member 360 also is a tubular member having a lumen 364 extending between the ends of the insertion member and the stop portion includes therein a through aperture 366 that communicates with the insertion member lumen. In use, the lumen 364 and the through aperture 366 comprises the entry aperture formed in the eye 2 through which the surgical instruments and the probe member 204 and ultrasonic transducer 206 introduced.

The inserted end 369 of the insertion member 360 is illustrated as being substantially flat. It is within the scope of the present invention, however, for the inserted end 369 to be pointed, cut on a bias or other wise configured so as to form a tissue piercing type of end.

In either of the illustrated embodiments, the probe member 204 is inserted into the intra-ocular volume of the eye until the ultrasonic transducer 206 is positioned proximal the retina. As noted above, in an illustrative embodiment, the ultrasonic transducer 206 is spaced about 0.5 mm from the surface of the retina. Thereafter, the handle member 202 is manipulated so as to cause the ultrasonic transducer 206 to scan an area or strip of the retina. The reflections from the tissue and/or anatomical structure of the eye are received by the transducer and outputted to the monitor 104 for viewing by the surgeon.

The use of such an entry alignment device 350a,b advantageously avoids the dissection of the conjunctiva 4 and its subsequent reattachment to the eye, a requirement of existing prior art surgical methods and techniques. The foregoing procedure, in conjunction with the instruments and devices used in conjunction with this procedure, reduce the size or make smaller the incisions that are made through the sclera 6 for the passage of instruments and infusion cannula, and thus reduce trauma to the eye. Further because there is no need to dissect and reattach the conjunctiva, the time required for the surgical procedure to be performed is reduced, thus also reducing the time the patient is on the operating table and the overall cost of the procedure. The entry alignment devices illustrated herein shall not be construed as a limitation, as it is within the scope of the present invention to utilize any of the entry alignment devices disclosed in U.S. Ser. No. 09/523,767.

Thus, the intra-operative microsurgical imaging device 200 of the present invention provides a mechanism or tool by which a surgeon or technician can scan the retina during the retinal repair procedure to evaluate the effectiveness of the actions taken. In other words, the surgeon can evaluate the effectiveness of the surgical procedure at any time during the procedure and thus has the ability to revise the planned actions to deal with any indications of less than effective results.

This capability to evaluate the effectiveness of a surgical procedure, while performing the procedure has a number of beneficial effects. Because the effectiveness of the procedure can be accomplished during the conduct of the procedure, the net effect is to reduce the chance that the subsequently performed diagnostic test will reveal a problem requiring a further surgical procedure(s). Consequently, the number of operations or procedures being performed should be reduced as compared to prior art techniques. This also should result in reductions in the amount of time a patient spends recovering as compared to prior art techniques.

In the foregoing, the use of the intra-operative microsurgical imaging device 200 of the present invention is illustrated in connection with a retinal tear repair procedure, this shall not be construed as imposing limitation on the usage of the imaging device for other microsurgical procedures. For example, the intra-operative microsurgical imaging device is contemplated for use in connection with middle ear surgery so that the imaging of the middle ear does not involve externalizing. Such an imaging device also is adaptable for diagnostic procedures involving the eye and for invasive diagnostic procedures or tests where there is a risk involved with placement of a test instrumentality and the imaging device can be used to reduce such risks. For example, diagnostic procedures or tests involving the use of needles to extract a tissue sample or extract a fluid sample (amniotic fluid).

Although a preferred embodiment of the invention has been described using specific terms, such description is for illustrative purposes only, and it is to be understood that changes and variations may be made without departing from the spirit or scope of the following claims.

What is claimed is:

1. A method for imaging a surgical site in an eye, comprising the steps of:
   providing an imaging device including a first member, a second grippable member, and an ultrasonic signal transmitting and receiving apparatus secured proximal one end of the first member;
   inserting the first member and the ultrasonic signal transmitting and receiving apparatus into an opening in the eye such that the ultrasonic signal transmitting and receiving apparatus is within close imaging proximity of the surgical site, while the second grippable member remains outside the eye;
   imaging the surgical site with the apparatus; and
   receiving the ultrasonic signals of the material at the surgical site to yield an image of the surgical site.

2. The method of claim 1, wherein the ultrasonic signals being transmitted and received are high frequency signals.

3. The method of claim 1, further comprising the step of supporting the ultrasonic signal transmitting and receiving apparatus remote from the surgical site.

4. The method of claim 3, wherein said supporting further includes providing a first member one portion of which being secured to the ultrasonic signal transmitting and receiving apparatus and another portion of which being secured remote from the surgical site.

5. The method of claim 1, further comprising the step of causing the ultrasonic signal transmitting and receiving apparatus to move along a predetermined path whereby a series of images are generated.

6. A microsurgical procedure for imaging a surgical site in an eye, comprising the steps of:
   determining a planned surgical approach for a patient;
   providing an imaging device including a first member, a second grippable member, and an ultrasonic signal transmitting and receiving apparatus;
   inserting the first member and the ultrasonic signal transmitting and receiving apparatus into an opening in the eye such that the ultrasonic signal transmitting and receiving apparatus is in close proximity to the surgical site to be imaged, while the second grippable member remains outside the eye;
   receiving ultrasonic signals reflecting from the material at the surgical site and processing the received signals so as to yield an image of the surgical site; and
   evaluating the image of the surgical site to determine if the planned approach should be modified.

7. The microsurgical procedure of claim 6, further including adjusting the planned approach when said evaluating determines that the planned approach should be modified.

8. The microsurgical procedure of claim 6, further comprising transmitting high frequency ultrasonic signals into material comprising the surgical site.

9. The microsurgical procedure of claim 6, wherein said evaluating is performed during the planned surgical approach.

10. The microsurgical procedure of claim 6, wherein the surgical site is a retina of an eye and wherein said locating includes locating the ultrasonic signal transmitting and receiving apparatus in close proximity to the retina.

11. The microsurgical procedure of claim 10, further comprising supporting the ultrasonic signal transmitting and receiving apparatus remote from the eye.

12. The microsurgical procedure of claim 11, further comprising remotely manipulating the ultrasonic signal transmitting and receiving apparatus so as to receive reflected signals from a plurality of locations of the retina.

13. The microsurgical procedure of claim 11, wherein said supporting includes providing a first member to support the ultrasonic signal transmitting and receiving apparatus remote from eye.

14. The microsurgical procedure of claim 6, further comprising supporting the ultrasonic signal transmitting and receiving apparatus remote from the surgical site.

15. The microsurgical procedure of claim 14, further comprising manipulating the ultrasonic signal transmitting and receiving apparatus from a location remote from the surgical site so as to receive reflected signals from a plurality of locations of the surgical site.

16. An intra-operative microsurgical device useable for imaging a surgical site in an eye before ending a microsurgical procedure, said device comprising:
   a first member;
   a second grippable member;
   an ultrasonic signal transmitting and receiving apparatus being secured to an end of the first member; and
   wherein the first member and the ultrasonic signal transmitting and receiving apparatus are configured and arranged to be inserted into an opening in the eye such that the ultrasonic signal transmitting and receiving apparatus is disposed in close proximity to the surgical site to be imaged while the second grippable member remains outside the eye.

17. The device of claim 16, wherein the ultrasonic transmitting and receiving apparatus is an ultrasonic transducer.

18. The device of claim 16, wherein the ultrasonic transmitting and receiving apparatus transmits and receives high frequency ultrasonic signals.

19. The device of claim 18, wherein the ultrasonic signals being transmitted and received are in a frequency range equal to or greater than about 50 mHz.

20. The device of claim 18, wherein the ultrasonic signals being transmitted and received are about 50 mHz.

21. The device of claim 16, wherein the first member has a length set so that the ultrasonic signal transmitting and receiving apparatus is disposed in close proximity to the surgical site such that ultrasonic signals being transmitted penetrate the material of the surgical site to obtain the desired image.

22. The device of claim 21, wherein the surgical site is a retina of an eye and wherein the length is set so the ultrasonic signal transmitting and receiving apparatus is disposed within close proximity to the retina.

23. The device of claim 22, wherein the ultrasonic signal transmitting and receiving apparatus is disposed within about 0.5 mm of the retina.

24. A method for treating a retinal tear or detachment in an eye comprising the steps of:
   providing an imaging device including a first member, an ultrasonic signal transmitting and receiving apparatus secured proximal one end of the first member, and a second grippable member secured to the other end of the first member;
   inserting the first member into the eye such that the one end and the ultrasonic signal transmitting and receiving apparatus are intra-ocular, and the second grippable member remains outside the eye; and
   further selectively inserting the first member so the ultrasonic signal transmitting and receiving apparatus is spaced about 0.5 mm from the surface of a retina of the eye such that transmitted signals penetrate at least the retina.

25. The method of claim 24, further comprising transmitting high frequency ultrasonic signals, and wherein said further selectively inserting includes further inserting the first member so the high frequency signals penetrate at least the retina.

26. The method of claim 24, further comprising evaluating received ultrasonic signals to determine if a surgical approach being executed should be modified.

27. The method of claim 26, further comprising adjusting the surgical approach when it is determined by said evaluating that the approach should be modified.

28. The method of claim 24 further comprising manipulating the first member such that the ultrasonic signal transmitting and receiving apparatus traverses a portion of a surface of the retina.

29. The method of claim 24 further comprising:

inserting an entry alignment device having a lumen into the eye so as to form an aperture through at least one of the conjunctiva and the sclera; and and wherein said inserting the first member includes passing the first member through the lumen.

30. A method for controlling the performance of a diagnostic procedure of an eye, comprising the steps of:

providing an imaging device including a first member, a second grippable member, and an ultrasonic signal transmitting and receiving apparatus secured proximal one end of the first member;

inserting the first member and the ultrasonic signal transmitting and receiving apparatus into an opening in the eye such that the ultrasonic signal transmitting and receiving apparatus is within close imaging proximity of a site to be subjected to the diagnostic procedure and the second grippable member remains outside the eye;

imaging the site with the apparatus;

receiving the ultrasonic signals of the material at the surgical site to yield an image of the site;

evaluating the image to determine if conditions at the site are acceptable for performing the diagnostic procedure;

wherein in the case where said evaluating determines that the conditions are acceptable said method includes proceeding with the diagnostic procedure; and wherein in the case where said evaluating determines that the conditions are not acceptable, said method includes not proceeding with the diagnostic procedure.

* * * * *